US00PP20779P2

(12) United States Plant Patent
Meilland

(10) Patent No.: US PP20,779 P2
(45) Date of Patent: Feb. 23, 2010

(54) MINIATURE ROSE PLANT NAMED 'MEILUDOCA'

(50) Latin Name: *Rosa hybrida*
Varietal Denomination: cv. Meiludoca

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 12/285,419

(22) Filed: Oct. 3, 2008

(51) Int. Cl.
*A01H 5/00* (2006.01)

(52) U.S. Cl. ..... Plt./119
(58) Field of Classification Search ..... Plt./119
See application file for complete search history.

*Primary Examiner*—Kent L Bell
(74) *Attorney, Agent, or Firm*—Buchanan Ingersoll & Rooney PC

(57) ABSTRACT

A new and distinct Miniature rose plant is provided which abundantly forms on a substantially continuous basis attractive bronze colored blossoms. Such blossoming commonly begins early in the season. A bushy growth habit is displayed that is well adapted for pot culture. The dense semi-glossy green foliage contracts nicely with the bronze colored blossom coloration. The tolerance to disease is good, particularly with respect to Oidium.

1 Drawing Sheet

Figures 1, 2, 3, 4, 5, 6, 7, 8, 9, 10, 11, 12, 13, 14, 15, 16, 17:
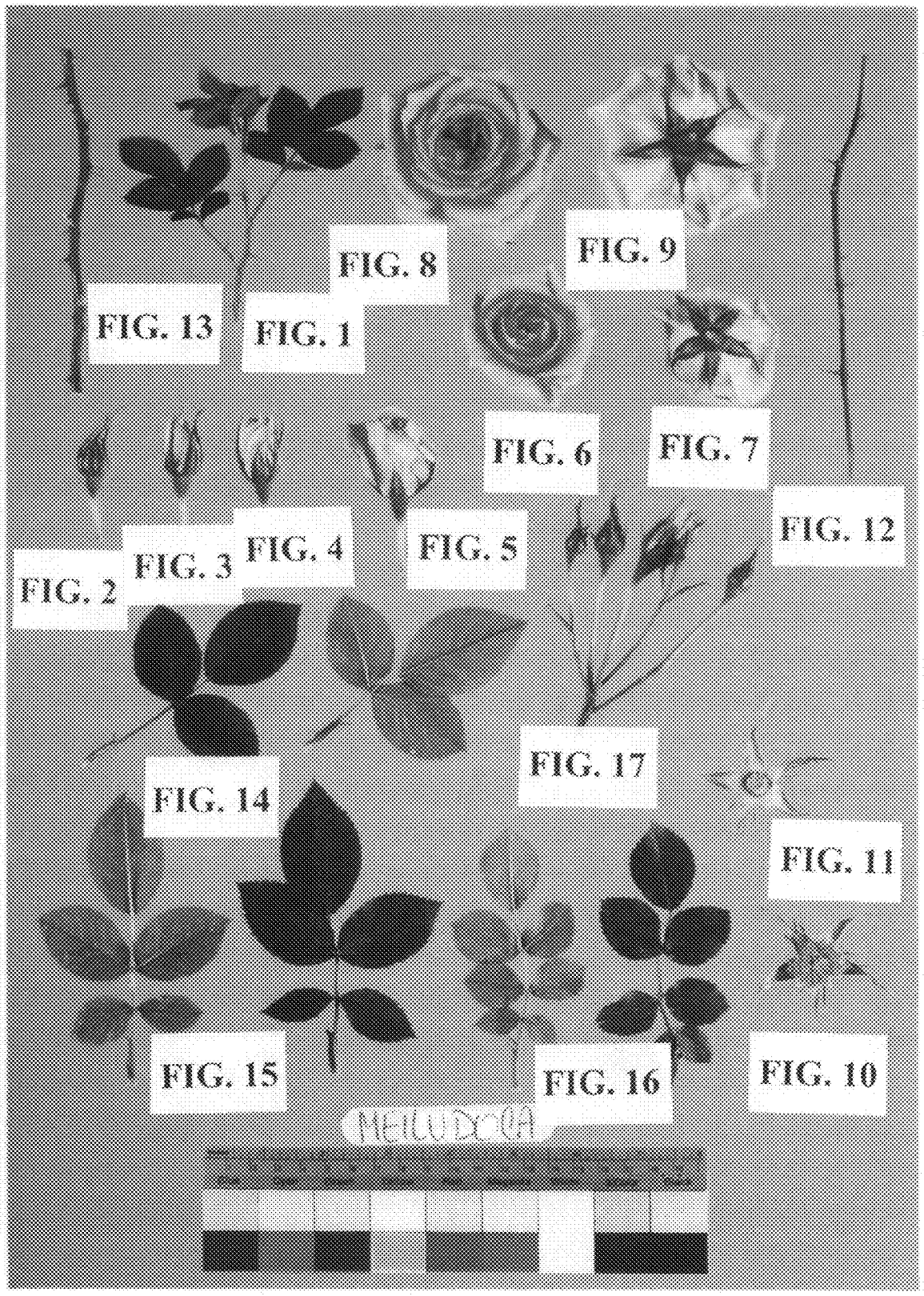

Botanical/commercial classification: *Rosa hybrida*/Miniature Rose Plant.

Vareital denomination: cv. Meiludoca.

SUMMARY OF THE INVENTION

The new variety of *Rosa hybrida* Miniature rose plant was created by artificial pollination wherein two parents were crossed which previously had been studied in the hope that they would contribute the desired characteristics. The female parent (i.e., the seed parent) of the new variety was the 'Meichanso' variety (non-patented in the United States). The 'Meichanso' variety is marketed under the PARADOR trademark. The male parent (i.e., the pollen parent) was the product of the cross of the 'Delpo' variety (non-patented in the United States) and the 'Savalife' variety (U.S. Plant Pat. No. 5,482). The 'Delpo' variety is marketed under the DIABLOTIN trademark and the 'Savalife' variety is marketed under the RAINBOW'S END trademark. The parentage of the new variety can be summarized as follows:

'Meichanso'×('Delpo'×'Savalife').

The seeds resulting from the above pollination were sown and small plants were obtained which were physically and biologically different from each other. Selective study resulted in the identification of a single plant of the new variety.

It was found that the new variety of Miniature rose plant of the present invention displays the following combination of characteristics:

(a) exhibits a bushy growth habit that is well adapted for pot culture, (b) abundantly forms on a substantially continuous basis attractive bronze colored blossoms, and (c) forms attractive dense semi-glossy green foliage.

The new variety flowers early and well meets the needs of the horticultural industry. It is particularly well suited for growing in pots as well as in the landscape. For instance, it can be grown to advantage along walkways and in mixed border plantings. The semi-glossy green foliage contrasts well with the bronze colored blossom coloration.

The new variety of the present invention can be readily distinguished from its ancestors. The flower coloration is different in each instance. More specifically, the 'Meichanso' variety forms geranium red flowers, the 'Delpo' variety forms light red flowers, and the 'Savalife' variety forms yellow flowers that are margined with red.

The new variety has been found to undergo asexual propagation in France by a number of routes, including budding, grafting, and cuttage. Asexual propagation by the above-mentioned methods as performed in the South of France has shown that the characteristics of the new variety are strictly transmissible from one generation to another.

The new variety has been named 'Meiludoca'.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately one year of age and were observed during April while growing outdoors on their own roots at LeCannet des Maures, Var, France. Dimensions in centimeters as well as a color comparison are shown at the bottom of the photograph.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower during the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates specimens of leaves with three leaflets—plan view—upper surface (left) and—under surface (right);

FIG. 15—illustrates specimens of leaves with five leaflets—plan view—under surface (left) and—upper surface (right);

FIG. 16—illustrates specimens of leaves with seven leaflets—plan view—under surface (left) and—upper surface (right); and FIG. 17—illustrates a cluster of buds.

DETAILED DESCRIPTION

The chart used in the identification of the colors is that of The Royal Horticultural Society (R.H.S. Colour Chart). The description is based on the observation of specimens of the new variety at an age of approximately one year which were observed during April while growing on their own roots outdoors at LeCannet des Maures, Var, France.

Class: Miniature.

Plant:

*Habit.*—Bushy.

*Height.*—Commonly approximately 30 to 35 cm on average.

*Width.*—Commonly approximately 25 to 30 cm on average.

Branches:

*Length.*—Commonly approximately 23 to 27 cm on average.

*Diameter.*—Commonly approximately 8 mm on average.

*Color.*—Young stems: near Green Group 143B. adult wood: near Green Group 137A.

*Thorns.*—Size and quantity: on young stems approximately 5 on average having a length of approximately 0.4 cm on average over a length of 10 cm, and on adult stems approximately 14 on average having a length of approximately 0.8 cm on average over a length of 18 cm. color: on young stems near Greyed-Orange Group 166D, and on adult stems near Greyed-Orange Group 174A. configuration: on young stems curved downwards and very longish pointed on the upper surface and hooked on the under surface with a narrow and short base, and on adult stems substantially upright and very longish pointed and slightly concave on the under surface with a narrow and short base.

Leaves:

*Petioles.*—Upper surface: non-glandular, and near Green Group 137D in coloration. under surface: commonly without prickles, and near Yellow-Green Group 14D in coloration. size: approximately 2.6 cm in length on average and approximately 1 mm in diameter on average on the terminal leaflet.

*Rachis.*—Upper surface: near Red Group 46A in coloration. under surface: smooth, and near Yellow-Green Group 146D in coloration. size: approximately 2.9 cm in length on average and approximately 0.5 mm in diameter.

*Stipules.*—Adnate, pectinate, narrow, approximately 1.7 cm in length on average, approximately 0.4 cm in width on average, near Green Group 143B on the upper surface, and near Green Group 141C on the under surface.

*Leaflets.*—Number: commonly 3 and 5. shape: oval, with an elongated pointed tip and a rounded base (as illustrated). texture: rather thick. serration: small and single. general appearance: dense and semi-glossy. size: terminal leaflets commonly measure approximately 3.6 cm in length on average and approximately 2 cm in width on average. color (young foliage): upper surface: near Green Group 143A. under surface: near Yellow-Green Group 146B. color (mature foliage): upper surface: near Green Group 137A. under surface: near Yellow-Green Group 146C.

Inflorescence

*Number of flowers.*—Commonly 1 flower per stem.

*Peduncle.*—Pubescent, near Greyed-Red Group 181A with Yellow-Green Group 144A in coloration, approximately 5 cm in length on average, and approximately 0.2 cm in diameter on average.

*Sepals.*—Number: five. upper surface: smooth, and near Greyed-Red Group 181B with Yellow-Green Group 148B in coloration. under surface: tomentose, and near Green Group 141C in coloration. shape: longish-pointed and narrow at the tip, and commonly three sepals bear some weak foliaceous extensions having lengths of up to approximately 7 mm. length: approximately 3 cm on average. width: approximately 0.7 cm on average.

*Buds.*—Shape: globular. size: approximately 2 cm in length on average, and approximately 1.8 cm in width on average. color: as the calyx breaks on the upper surface near Orange-Red Group 30B, and on the under surface near Yellow-Orange Group 23C and suffused with near Orange Group 25B and Orange-Red Group 33B.

*Flower.*—Form: cup-shaped. diameter: commonly approximately 5 cm on average when fully open. depth: commonly approximately 2.4 cm on average when fully open. color (during the course of opening): upper surface: near Orange Group 28A suffused with near Orange Group 28B, and with a small spot of near Yellow Group 5A at the base. under surface: near Orange Group 23B, suffused with near Orange Group 29A and near Orange-Red Group 33B, and with a small spot of Yellow Group 3A at the base. color (when open): upper surface: near Orange-Red Group 31A and slightly veined with Yellow-Orange Group 23C, and with a small spot of Yellow Group 5A at the base. under surface. near Yellow-Orange Group 21C amply suffused with Orange Group 26C, and with a small spot of Yellow Group 3A at the base. fragrance: none. anthers: near Yellow-Orange Group 17A in coloration, regularly arranged around the styles, and approximately 0.3 cm in length on average. stamen number: approximately 147 on average. filaments: near Yellow Group 2C in coloration, and approximately 0.5 cm in length on average. pollen: present. pistil number: approximately 113 on average. stig mas: near Yellow Group 2D in coloration, and approximately 0.2 cm in diameter on average. styles: near Green-Yellow Group 150D in coloration, and approximately 0.4 cm in length. petal number: approximately 26 on average under normal growing conditions. petal arrangement: imbricated. petal shape: with a rounded tip and a rounded base. petal margin: commonly reflexed. petal size: commonly approximately 2.9 cm in length on average, and approximately 3 cm in width on average. petal texture: rather thick. petal drop: good, the petals commonly detach cleanly before drying. petaloids: small in size and commonly present towards the blossom center. receptacle: commonly smooth, near Yellow Group 143B in coloration, and pitcher-shaped in cross section, approximately 0.8 cm in length on average, and approximately 0.4 cm in width on average.

Development:

*Vegetation.*—Medium strong.

*Blooming.*—Very early, abundant, and substantially continuous.

*Tolerance to diseases.*—Good, especially with respect to Oidium.

I claim:

1. A new and distinct variety of Miniature rose plant characterized by the following combination of characteristics:

(a) exhibits a bushy growth habit that is well adapted for pot culture, (b) abundantly forms on a substantially continuous basis attractive bronze colored blossoms, and (c) forms attractive dense semi-glossy green foliage; substantially as herein shown and described.

* * * * *